(12) United States Patent
Whelan et al.

(10) Patent No.: US 12,416,637 B2
(45) Date of Patent: Sep. 16, 2025

(54) BIOMARKERS FOR IRRITABLE BOWEL SYNDROME

(71) Applicants: THE UNIVERSITY OF LIVERPOOL, Liverpool (GB); KING'S COLLEGE LONDON, London (GB)

(72) Inventors: Kevin Whelan, London (GB); Bridgette Wilson, London (GB); Megan Rossi, London (GB); Chris Probert, Liverpool (GB); Rachael Slater, Liverpool (GB)

(*) Notice: Subject to any disclaimer, the term of this patent is extended or adjusted under 35 U.S.C. 154(b) by 932 days.

(21) Appl. No.: 17/624,295

(22) PCT Filed: Jul. 3, 2020

(86) PCT No.: PCT/GB2020/051604
§ 371 (c)(1),
(2) Date: Dec. 31, 2021

(87) PCT Pub. No.: WO2021/005341
PCT Pub. Date: Jan. 14, 2021

(65) Prior Publication Data
US 2022/0357333 A1      Nov. 10, 2022

(30) Foreign Application Priority Data

Jul. 5, 2019 (GB) ..................................... 1909709

(51) Int. Cl.
*G01N 33/50* (2006.01)
*G01N 33/64* (2006.01)

(52) U.S. Cl.
CPC ....... *G01N 33/64* (2013.01); *G01N 2800/065* (2013.01)

(58) Field of Classification Search
None
See application file for complete search history.

(56) References Cited

U.S. PATENT DOCUMENTS

| | | |
|---|---|---|
| 7,306,953 B2 | 12/2007 | Probert et al. |
| 2012/0309048 A1 | 12/2012 | Ratcliffe et al. |
| 2018/0038839 A1 | 2/2018 | Probert et al. |

FOREIGN PATENT DOCUMENTS

| | | |
|---|---|---|
| WO | 2004008953 | 1/2004 |
| WO | 2012127213 | 9/2012 |

OTHER PUBLICATIONS

United Kingdom Search Report prepared for United Kingdom Patent Application No. 1909709.6, completed Dec. 10, 2019.
PCT Search Report and Written Opinion prepared for PCT Application No. PCT/GB2020/051604, completed Sep. 15, 2020.
Ahmed, et al., "An Investigation of Fecal Volatile Organic Metabolites in Irritable Bowel Syndrome," Mar. 1, 2013, Public Library of Science, vol. 8, Nr: 3, pp. 1-13.
Rossi, et al., "Volatile Organic Compounds in Feces Associate With Response to Dietary Intervention in Patients With Irritable Bowel Syndrome." 2018, Clinical Gastroenterology and Hepatology, No. 16, pp. 385-391.
Aras Aradnam, R.P. et al., "Differentiating Coeliac Disease from Irritable Bowel Syndrome by Urinary Volatile Organic Compound Analysis—A Pilot Study," PLOSone, 2014, 9(10) pp. 1-9.
Baranska, A. et al., "Volatile organic compounds in breath as markers for irritable bowel syndrome: a metabolomic approach," Alimentary Pharmacology and Therapeutics, 2016, vol. 44, pp. 45-56.
Bosch, S. et al., "Differentiation Between Pediatric Irritable Bowel Syndrome and Inflammatory Bowel Disease Based on Fecal Scent: Proof of Principle Study," Inflamm Bowel Dis. 2018, 24(11) pp. 2468-2475.
Buijck, M. et al., "Sniffing Out Paediatric Gastronintestinal Diseases: The Potential of Volatile Organic Compounds as Biomarkers for Disease," JPGN, 2016, 63(6) pp. 585-591.
Camilleri, M. et al., "Validating Biomarkers of Treatable Mechanisms in Irritable Bowel Syndrome," Neurogastroenterol Motil., 2014, 26(12) pp. 1677-1685.
Hicks, L.C. et al., "Analysis of Exhaled Breath Volatile Organic Compounds in Inflammatory Bowel Disease: A Pilot Study," Journal of Crohn's and Colitis, 2015, 731-37.
Kim, J.H.K., "Biomarkers of Irritable Bowel Syndrome," J. Neurogastroenterol Mostil., 2017, 23(1) pp. 20-26.
Li, X-G. et al., "Fecal calprotectin in differential diagnosis of irritable bowel syndrome," Journal of Peking University (Health Sciences), 2006, 38(3) pp. 310-313 (abstract only).
Mujagic, Z. et al., "A novel biomarker panel for irritable bowel syndrome and the application in the general population," Scientific Reports, 2016, 6(26420) pp. 1-10.
Probert, C. et al., "Volatile Organic Compounds as Diagnostic Biomarkers in Gastrointestinal and Liver Diseases," J. Gastrointestin Liver Dis., 2009, 18(3) pp. 337-343.
Reade, S. et al., "Potential role of fecal volatile organic compounds as biomarkers of chemically induced intestinal Inflammation in mice," The FASEB Journal, 2019 vol. 33, pp. 1-9.
Rossi. M. et al., "Volatile Organic Compounds Predict Response to Both Low Fodmap Diet and Probiotics in Irritable Bowel Syndrome: a Randomised Controlled Trial," AGA Abstracts, Mol. 1547, pp. S-713 to S-714.
Sood, R. and Ford, A.C., "Editorial: volatile organic compounds in irritable bowel syndrome—technology for an accurate and reliable point-of-care test?" Aliment Pharmacol Ther., 2017, vol. 45, pp. 563-564.

*Primary Examiner* — Christopher M Gross
(74) *Attorney, Agent, or Firm* — Barnes & Thornburg LLP

(57) ABSTRACT

The present invention relates to a method of determining the probability that an individual has irritable bowel syndrome and whether the individual will respond to dietary intervention. The present invention also provides a method of determining the probability that an individual with irritable bowel syndrome will respond to dietary intervention. There is also provided the use of a compound as defined herein as a biomarker.

20 Claims, 4 Drawing Sheets

BIOMARKERS FOR IRRITABLE BOWEL SYNDROME

CROSS-REFERENCE TO RELATED APPLICATIONS

This application is the U.S. national phase of PCT/GB2020/051604, filed on Jul. 3, 2020, which claims the benefit of United Kingdom Patent Application Serial Number 1909709.6, filed on Jul. 5, 2019, the entire disclosures of both of which are incorporated herein by reference.

FIELD OF THE DISCLOSURE

The present invention relates to a method of determining the probability that an individual has irritable bowel syndrome and whether that individual will respond to dietary intervention. The present invention also relates to a method of determining the probability that an individual suffering with irritable bowel syndrome will respond to dietary intervention. The present invention also relates to the use of a cyclohexane carboxylic acid compound as a biomarker to determine the likelihood of an individual with irritable bowel syndrome responding to a dietary intervention.

BACKGROUND

Irritable Bowel Syndrome (IBS) is a common condition that affects the digestive system. It is characterised by recurrent symptoms such as stomach cramps, abdominal pain, bloating, diarrhoea and/or constipation. These symptoms tend to come and go over time, but they can last for hours, days, weeks or even months at a time. It can be a life-long problem for many sufferers.

IBS is one of the most commonly diagnosed medical disorders in the developed world. It is estimated that up to 20% of the adult population can have one or more symptoms of IBS. The diagnosis of IBS is often based on an assessment of the symptoms and their frequency. There is currently no cure for IBS, so the treatment focuses on approaches to relieve and manage the symptoms. Some patients suffering with IBS can manage their symptoms (e.g. cramping, abdominal pain, bloating, constipation and diarrhoea) effectively by dietary management, stress management and/or medication. However, for many patients IBS can be an extremely disabling condition, impacting on their ability to work, attend social events, and/or travel (even short distances).

In terms of dietary intervention, a diet known as a low "FODMAP" diet has been shown to be of benefit in some IBS patients. The idea of the diet is to avoid food items that contain FODMAP compounds (Fermentable Oligosaccharides, Disaccharides, Monosaccharides And Polyols). However, it is currently difficult to predict which IBS patients will benefit from this dietary intervention.

There is, therefore, a need for improved methods for diagnosing IBS and for determining whether a patient suffering with IBS will respond to dietary intervention. The present invention was devised with the foregoing in mind.

BRIEF SUMMARY OF THE DISCLOSURE

In a first aspect of the invention there is provided a method of determining the probability that an individual has irritable bowel syndrome and whether the individual will respond to dietary intervention, the method comprising the steps of:

i) analysing a stool sample collected from said individual to determine whether a cyclohexane carboxylic acid compound is present; and ii) if a cyclohexane carboxylic acid compound is present in step i), determining the amount of the cyclohexane carboxylic acid compound that is present and comparing the amount detected with a control value;

wherein the presence of an increased amount of the cyclohexane carboxylic acid compound compared to the control value is indicative of an increased probability that the individual has irritable bowel syndrome and of the probability that the individual will respond to dietary intervention; and wherein the cyclohexane carboxylic acid compound is one or more of a cyclohexane carboxylic acid and/or a cyclohexane carboxylic acid ester.

The inventors have surprisingly found that detecting the presence of increased levels of the cyclohexane carboxylic acid compounds defined herein emanating from a stool sample (relative to a control value) enabled the determination of: (i) the probability of whether an individual has irritable bowel syndrome (IBS); and (ii) the probability of whether that individual would respond to dietary intervention. It has not previously been possible to determine which patients with IBS will respond to dietary intervention, so the identification of the cyclohexane carboxylic acid compounds defined herein as faecal biomarkers for determining the probability that an individual has IBS and whether they will respond to dietary intervention is a major advance. The method of the present invention therefore represents a significant improvement over existing methods.

In another aspect there is provided a method of determining the probability that an individual with irritable bowel syndrome will respond to dietary intervention, the method comprising the steps of:

i) analysing a stool sample collected from said individual to determine whether a cyclohexane carboxylic acid compound is present; and ii) if a cyclohexane carboxylic acid compound is present in step i), determining the amount of the cyclohexane carboxylic acid compound that is present and comparing the amount detected with a control value;

wherein the presence of an increased amount of the cyclohexane carboxylic acid compound compared to the control value is indicative of an increased probability that the individual will respond to dietary intervention; and wherein the cyclohexane carboxylic acid compound is one or more of a cyclohexane carboxylic acid and/or a cyclohexane carboxylic acid ester.

Suitably, the cyclohexane carboxylic acid compound is selected from one or more of cyclohexane carboxylic acid and/or a cyclohexane carboxylic acid (1-5 C)alkyl ester.

Suitably, the cyclohexane carboxylic acid compound is cyclohexane carboxylic acid and/or a cyclohexane carboxylic acid (1-4 C)alkyl ester.

Suitably, the cyclohexane carboxylic acid compound is selected from cyclohexane carboxylic acid, cyclohexane carboxylic acid methyl ester, cyclohexane carboxylic acid ethyl ester, cyclohexane carboxylic acid propyl ester, and cyclohexane carboxylic acid butyl ester. More suitably, the cyclohexane carboxylic acid compound is selected from cyclohexane carboxylic acid ethyl ester, cyclohexane carboxylic acid propyl ester and cyclohexane carboxylic acid butyl ester.

Suitably, the step of analysing the stool sample involves detecting whether two or more cyclohexane carboxylic acid compounds are present. The carboxylic acid compounds may be any of the carboxylic acid compounds described herein.

Suitably, the presence and amount of the cyclohexane carboxylic acid compound is determined by detecting volatile organic compounds (i.e. the volatile cyclohexane carboxylic acid compounds defined herein) emanating from the stool sample, e.g. by using gas chromatography mass spectrometry (GC-MS).

Suitably, in the methods of the present invention, the individual has one or more symptoms associated with irritable bowel syndrome. The one or more symptoms associated with irritable bowel syndrome may include one or more of diarrhoea, constipation, abdominal cramps, bloating and abdominal pain. The individual may have irritable bowel syndrome as defined by Rome III criteria. Rome III criteria is defined as symptoms persisting for at least three months, with onset at least six months previously, of recurrent abdominal pain or discomfort associated with two or more of the following: improvement with defecation; and/or onset associated with a change in frequency of stool; and/or onset associated with a change in form (appearance) of stool.

In the methods of the present invention, the control value typically is the amount of a carboxylic acid compound detectable from stool samples from an individual or cohort of individuals that are non-dietary responders. The non-dietary responders may be an individual or cohort of individuals, with or without IBS, that does not respond to dietary intervention as defined herein. The non-dietary responders may be an individual or cohort of individuals with IBS that does not respond to dietary intervention. The non-dietary responders may be an individual or cohort of individuals without IBS that does not respond to dietary intervention.

The dietary intervention may include one or more of a low wheat diet, a low oligosaccharides, a low disaccharides diet, a low monosaccharides diet, a low polyol diet and/or a low FODMAP diet. The dietary intervention may include a low wheat diet or a low FODMAP diet. Suitably, the dietary intervention includes or consists of a low FODMAP diet. The dietary intervention may include further supplementation, e.g. with a pre- or pro-biotic.

In another aspect, there is provided the use of a cyclohexane carboxylic acid compound as a biomarker to determine the likelihood of an individual with irritable bowel syndrome responding to a dietary intervention. Suitably, the cyclohexane carboxylic acid compound is one or more of a cyclohexane carboxylic acid and/or a cyclohexane carboxylic acid ester.

Suitably, the cyclohexane carboxylic acid compound is any of the cyclohexane carboxylic acid compounds described herein, i.e. a cyclohexane carboxylic acid or a cyclohexane carboxylic acid alkyl ester. Suitably, the cyclohexane carboxylic acid compound is selected from cyclohexane carboxylic acid, cyclohexane carboxylic acid methyl ester, cyclohexane carboxylic acid ethyl ester, cyclohexane carboxylic acid propyl ester, cyclohexane carboxylic acid butyl ester and cyclohexane carboxylic acid pentyl ester.

BRIEF DESCRIPTION OF THE DRAWINGS

Embodiments of the invention are further described hereinafter with reference to the accompanying drawings, in which:

Referring to FIG. 4, in the top line, A0 (light blocks) are non-responders, A1 (dark blocks) are responders to the low FODMAP diet. The three rows below the top row illustrate the relative abundance (light=low, dark=high) of the cyclohexane carboxylic acid compounds most of which are higher in responders than non-responders (36.43 is cyclohexane carboxylic acid, butyl ester; 30.27 is cyclohexane carboxylic acid, ethyl ester; 33.47 is cyclohexane carboxylic acid, propyl ester). The vertical labels at the bottom are sample identifiers.

DETAILED DESCRIPTION

Figure 1:
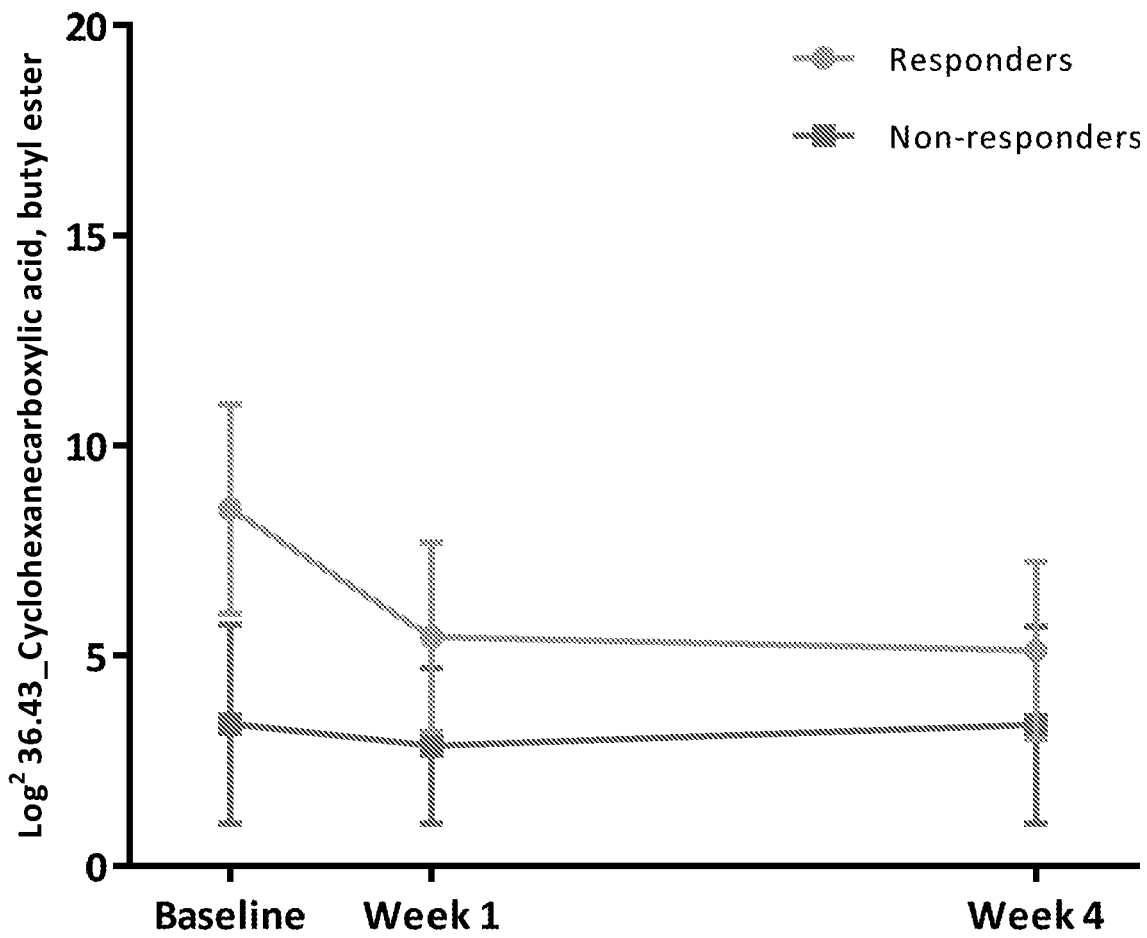
FIG. 1 shows mean (SD) $\log^2$ values for faecal cyclohexane carboxylic acid butyl ester in the LFD group comparing responders (n=10) and non-responders (n=9) at baseline, week-1 and week-4.
Figure 2:
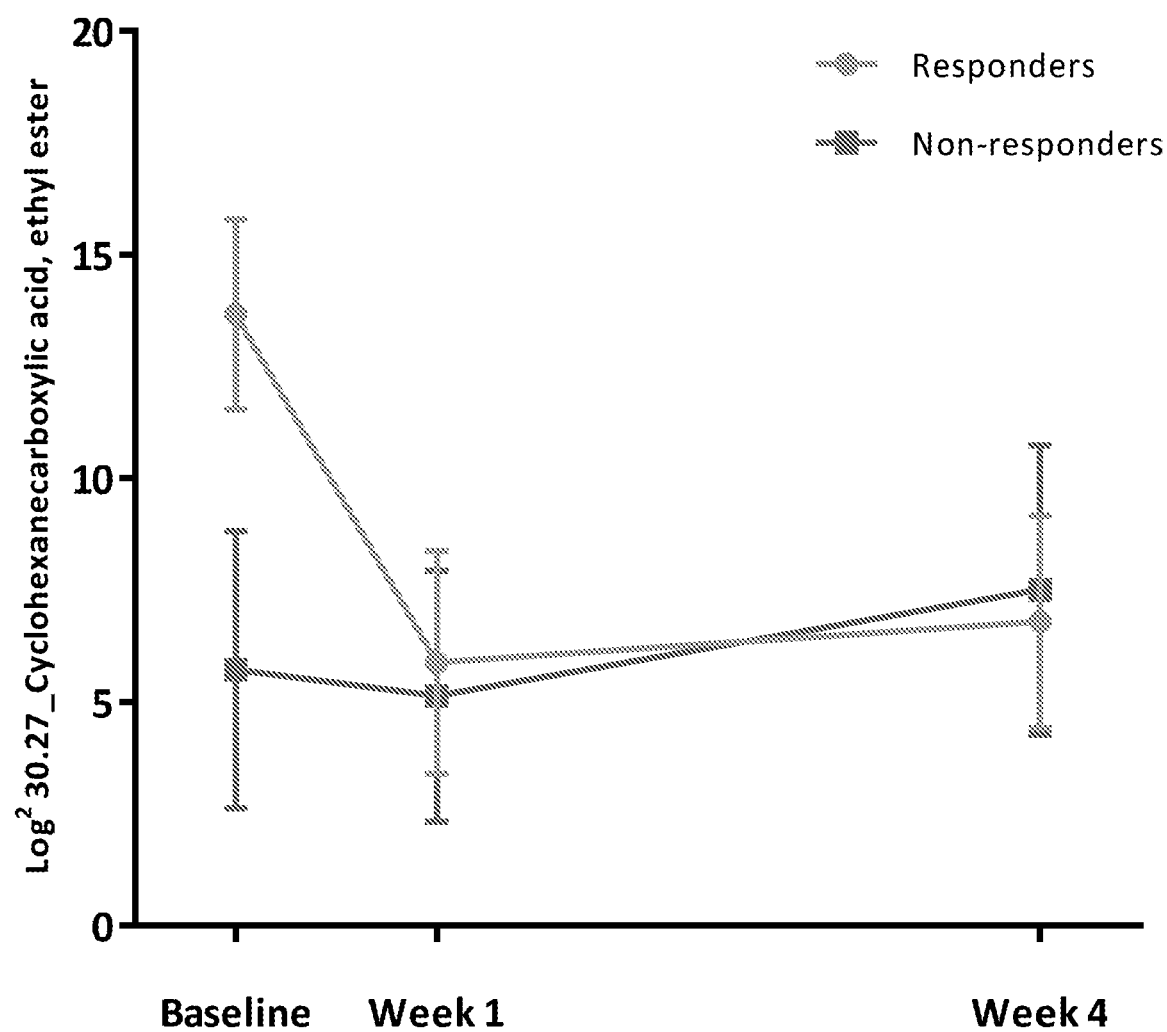
FIG. 2 shows mean (SD) $\log^2$ values for faecal cyclohexane carboxylic acid ethyl ester in the LFD group comparing responders (n=10) and non-responders (n=9) at baseline, week-1 and week-4.
Figure 3:
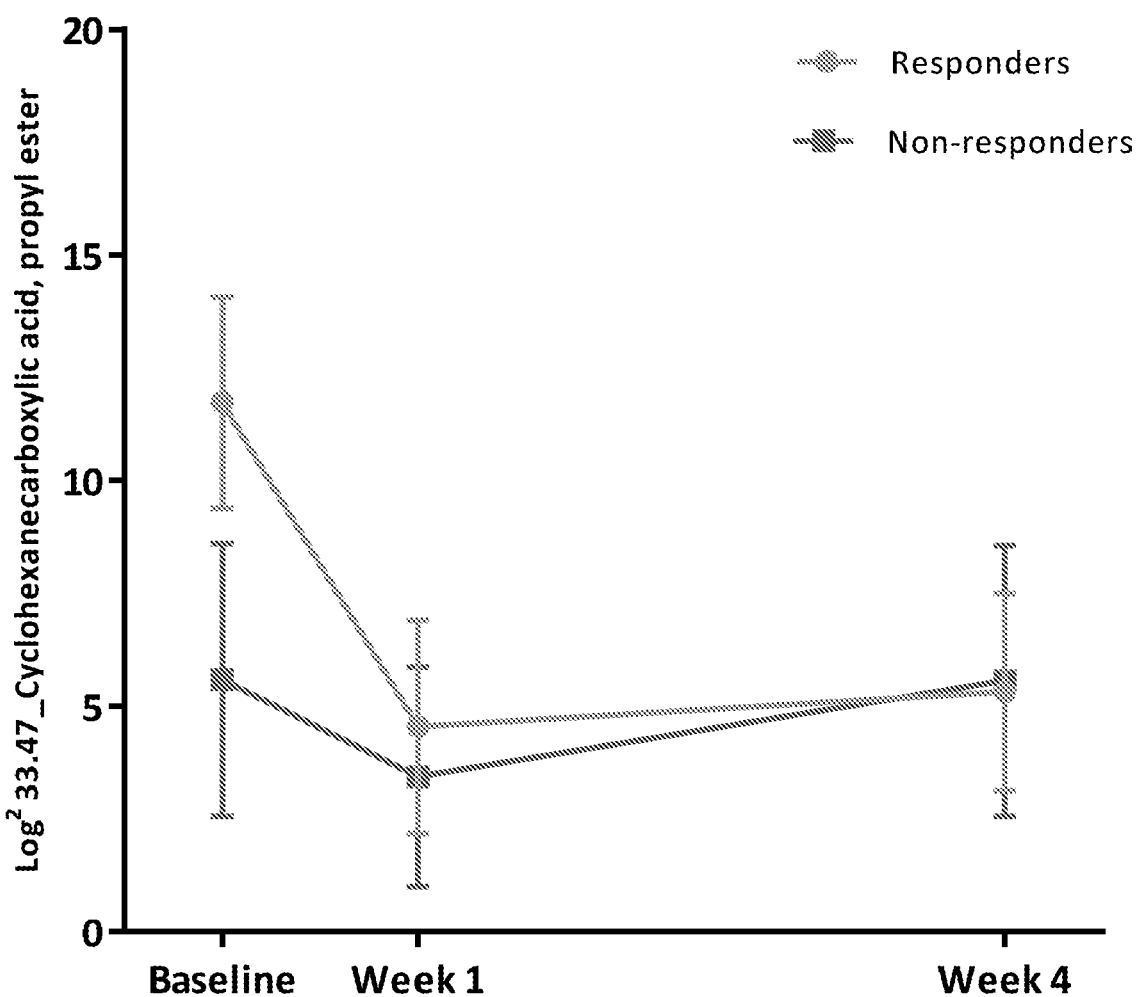
FIG. 3 shows mean (SD) $\log^2$ values for faecal cyclohexane carboxylic acid propyl ester in the LFD group comparing responders (n=10) and non-responders (n=9) at baseline, week-1 and week-4.

The term FODMAP is derived from "Fermentable, Oligo-, Di-, Monosaccharides, and Polyols". FODMAPs are short chain carbohydrates and monosaccharides which are poorly absorbed in the small intestine. The main dietary sources of the four groups of FODMAPs include:

Oligosaccharides: Wheat, rye, legumes and various fruits and vegetables, such as garlic and onions.

Disaccharides: Milk, yogurt and soft cheese. Lactose is the main carbohydrate associated with such foods.

Monosaccharides: Various fruit including figs and mangoes, and sweeteners such as honey and agave nectar. Fructose is the main carbohydrate associated with such foods.

Polyols: Certain fruits and vegetables including blackberries and lychee, as well as some low-calorie sweeteners like those in sugar-free gum.

It will be understood from the context of the present invention that the carboxylic acid compounds described herein are volatile organic compounds. A "volatile organic compound" may be thought of as an organic compound having an initial boiling point less than or equal to 250° C. (482° F.) measured at a standard atmospheric pressure of 101.3 kPa.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Stool Volatile Organic Compounds

Volatile organic compound (VOC) analysis was performed using gas-chromatography mass-spectrometry (GC-MS) on a PerkinElmer Clarus 500 GC/MS quadrupole benchtop system (Beaconsfield, UK) and Combi PAL autosampler (CTC Analytics, Switzerland) for all stool samples collected at baseline, week-1 and week-4 for all participants.

Volatile organic compounds (VOCs) are intermediaries/endpoints of metabolic pathways and are reflective of colonic metabolism [1]. There are a large number of VOCs within human stool and the VOC profile as well as individual VOCs have been shown in one study to be different between responders and non-responders to the Low FODMAP diet [2].

250-300 μg of each sample was weighed into 2 ml glass vials with magnetic septum caps (Crawford Scientific, Lanarkshire, UK) and the GC-MS was conducted. The solid phase micro-extraction fibre used was a DVB-CAR-PDMS otherwise the protocol was the same as published by Reade et al (2014) [1].

Volatile Organic Compound Extraction Protocol

The GC column used was a Zebron ZB-624 with inner diameter 0.25 mm, length 60 m, film thickness 1.4 μm (Phenomenex, Macclesfield, UK). The carrier gas used was helium of 99.996% purity (BOC, Sheffield, UK). The SPME fibre used was a DVB-CAR-PDMS 30 μm (1 cm) (Sigma-Aldrich, Dorset, UK). The fibre was pre-conditioned before use, in accordance with the manufacturer manual. Samples were pre-incubated for 30 mins at 60° C. prior to fibre exposure, the fibre was exposed to 60° C. for 20 mins then desorbed for 5 mins at 220° C. The initial temperature of the GC oven was set at 40° C. and held for 1 min before increasing to 220° C. at a rate of 5° C./min and held for 4 mins with a total run time of 41 mins. A solvent delay was set for the first 6 mins and the MS was operated in electron impact ionization EI+ mode, scanning from ion mass fragments 10 to 300 m/z with an interscan delay of 0.1 sec and a resolution of 1000 at FWHM (Full Width at Half Maximum). The helium gas flow rate was set at 1 ml/min. The sensitivity of the instrument was determined with 2-pentanone only and varies for other compounds. The limit of detection, as being 3 times the signal/noise ratio, of the method for 2-pentanone with DVB-CAR-PDMS is 16 ppm.

Test Protocol

VOC Levels in Responders Vs Non-Responders

Figure 4:
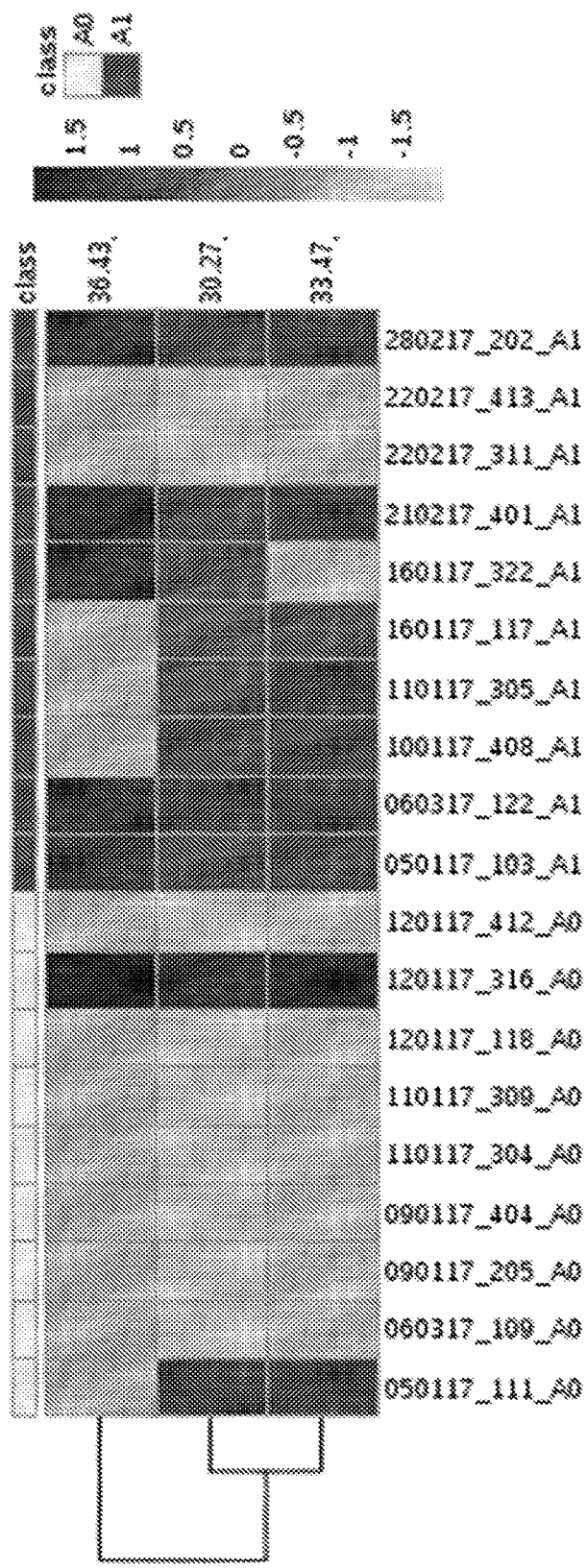
FIG. 4 shows a heat map displaying different faecal volatile organic compounds detected in responders compared to non-responders to the LFD.

When individual VOCs were compared using a heat map to visualise the differences between responders and non-responders at baseline a pattern was clear for a separation between responders and non-responders to the LFD at baseline (FIG. 4). This revealed a specific class of related VOC species that were higher in responders than non-responders at baseline. In general, patients responded to diet if they had higher levels of cyclohexane carboxylic acid butyl ester, cyclohexane carboxylic acid ethyl ester, and cyclohexane carboxylic acid propyl ester at baseline. There were exceptions to this rule: two patients did not respond to diet although both had high levels of the cyclohexanone acids at baseline and two patients had low levels of cyclohexanone acids but did respond to diet.

At baseline responders had higher log abundance (mean (SD)) of cyclohexane carboxylic acid ethyl ester (13.7 (2.1)) than non-responders (5.7 (3.1)), higher cyclohexane carboxylic acid propyl ester (11.73 (2.35)) than non-responders (5.59 (3.02)) and higher cyclohexane carboxylic acid butyl ester (8.49 (2.50)) than non-responders (3.37 (2.37)) (FIGS. 1-4) although these differences were not significant, possibly due to over-stringency of the statistical modelling being applied for direct two-group comparison. To further explore if the cyclohexane carboxylic acid family could predict response to the LFD, ROC curves were generated combining the three cyclohexane carboxylic acid compounds that were higher in responders at baseline compared to response (AUC=0.793 (fair), 95% Cl 0.5, 1 p>0.05). When only cyclohexane carboxylic acid, ethyl ester was checked against response it was able to predict response to the LFD at baseline with good specificity and sensitivity (AUC=0.854 (good), 95% Cl 0.542, 1, p=0.045).

Data Processing

The GCMS data were processed using a pipeline involving the Automated Mass Spectral Deconvolution and Identification System software (AMDIS, Version 2.71, 2012), the NIST mass spectral library (version 2.0, 2011) and the R (R core team, 2013) package Metab (Aggio R, Villas-Bôas SG, Ruggiero K. Metab: an R package for high-throughput analysis of metabolomics data generated by GC-MS. *Bioinformatics* 2011; 27:2316-8. doi:10.1093/bioinformatics/btr379). AMDIS and NIST software were used to build a VOC library containing the metabolites present in the stool samples analysed in this study. A forward and reverse match of 800/1000 and above was used for assigning tentative compound identifications. Using this VOC library, AMDIS was then applied to deconvolute chromatograms and identifying metabolites. The report generated by AMDIS was further processed by Metab, in order to align metabolites and recalculate their relative abundances based on the intensity of a specific ion mass fragment per metabolite. Compounds were named using IUPAC nomenclature.

Statistical Analysis

Data analysis was performed in R and Metaboanalyst (Xia, J., Sinelnikov, I., Han, B., and Wishart D. MetaboAnalyst 3.0—making metabolomics more meaningful. *Nucleic acid Res* 2015; 43: W251-7), utilising Student's t test, false discovery rate correction, Partial Least Squared Discriminant Analysis (PLS-DA), factor analysis and Receiver Operator Characteristic (ROC) analysis. When Metaboanalyst was used the data was normalised by median and log transformed.

Responder Vs Non-Responder Discussion

The separation of the cyclohexane carboxylic acid compound species between responders and non-responders at baseline in the LFD group is an interesting finding as VOC's have been shown to be able to differentiate between different GI conditions (Healthy control, IBS and IBD) and differential expression of VOCs in IBS and IBD normalise to healthy control following treatment to reduce disease activity or symptom severity respectively [4-6]. A study comparing VOC profiles in IBS patients that responded (37/46, 80%) (defined as a ≥50 point reduction on the IBS-SSS) to non-responders (9/46, 20%) to the LFD used a gas chromatography sensor device (Odoreader) to analyse faecal VOC profiles [2]. The VOC profiles were able to accurately distinguish between responders and non-responders at baseline with a mean accuracy of 97% (95% Cl, 96%-99%) although the method of analysis did not allow for individual VOC's to be identified. The current study builds on this evidence as the addition of mass spectrometry allows the identification of specific metabolites. The finding that related VOCs (the cyclohexane carboxylic acid compounds) distinguish responders from non-responders and that the LFD leads to a normalisation of this distinguishing factor provides an intriguing target for future research into the mechanism and prediction of response to the LFD.

TABLE 1

Mean fold change in faecal volatile organic compounds with >1-fold difference between responders and non-responders to the LFD.

| LFD | Fold Change ($\log^2$) |
| --- | --- |
| 36.43_Cyclohexane carboxylic acid, butyl ester | −1.4491 |
| 30.27_Cyclohexane carboxylic acid, ethyl ester | −1.3934 |
| 33.47_Cyclohexane carboxylic acid, propyl ester | −1.2087 |
| 17.98_2-Hexanone | 1.0657 |
| 25.22_Dimethyl trisulfide | 1.0438 |
| 15.92_Disulfide, dimethyl | 1.0251 |
| 14.06_Propanoic acid, ethyl ester | −1.0178 |

Data are presented as log2 mean fold change between responders and non-responders. Only VOC with mean fold change >1 are displayed.
Negative values = lower value in non-responders, positive value = higher value in non-responders 1. Reade, S., et al., *Optimisation of sample preparation for direct SPME-GC-MS analysis of murine and human faecal volatile organic compounds for metabolomic Studies.* Journal of Analytical & Bioanalytical Techniques, 2014. 5(2): p. 1.
2. Rossi, M., et al., *Volatile Organic Compounds in Feces Associate With Response to Dietary Intervention in Patients With Irritable Bowel Syndrome.* Clinical Gastroenterology and Hepatology, 2018. 16(3): p. 385-+.
3. Halmos, E., et al. *Diets that differ in their FODMAP content alter the colonic luminal microenvironment.* Gut, 2014. 64, 93-100 DOI: 10.1136/gutjnl-2014-307264.
4. Walton, C., et al., *Analysis of volatile organic compounds of bacterial origin in chronic gastrointestinal diseases.* Inflamm Bowel Dis, 2013. 19(10): p. 2069-78.
5. Ahmed, I., et al., *Investigation of faecal volatile organic metabolites as novel diagnostic biomarkers in inflammatory bowel disease.* Alimentary Pharmacology & Therapeutics, 2016. 43(5): p. 596-611.
6. Ahmed, I., et al., *An Investigation of Fecal Volatile Organic Metabolites in Irritable Bowel Syndrome.* Plos One, 2013. 8(3).

The invention claimed is:

1. A method of determining the probability that an individual has irritable bowel syndrome and whether the individual will respond to dietary intervention, the method comprising the steps of:
   i) analysing a stool sample collected from said individual to determine whether a cyclohexane carboxylic acid compound is present; and
   ii) if a cyclohexane carboxylic acid compound is present in step i), determining the amount of the cyclohexane carboxylic acid compound that is present and comparing the amount detected with a control value;
   wherein the presence of an increased amount of the cyclohexane carboxylic acid compound compared to the control value is indicative of an increased probability that the individual has irritable bowel syndrome and of the probability that the individual will respond to dietary intervention; and wherein the cyclohexane carboxylic acid compound is one or more of a cyclohexane carboxylic acid and/or a cyclohexane carboxylic acid ester.

2. The method according to claim 1, wherein the cyclohexane carboxylic acid compound is cyclohexane carboxylic acid and/or a cyclohexane carboxylic acid (1-4C) alkyl ester.

3. The method according to claim 1, wherein the cyclohexane carboxylic acid compound is selected from cyclohexane carboxylic acid methyl ester, cyclohexane carboxylic acid ethyl ester, cyclohexane carboxylic acid propyl ester, and cyclohexane carboxylic acid butyl ester.

4. The method according to claim 3, wherein the cyclohexane carboxylic acid compound is selected from cyclohexane carboxylic acid ethyl ester, cyclohexane carboxylic acid propyl ester and cyclohexane carboxylic acid butyl ester.

5. The method according to claim 1, wherein the step of analysing the stool sample involves detecting whether two or more cyclohexane carboxylic acid compound are present.

6. The method according to claim 1, wherein the presence and amount of the cyclohexane carboxylic acid compound is determined by detecting volatile organic compounds emanating from the stool sample using gas chromatography mass spectrometry (GC-MS).

7. The method according to claim 1, wherein the individual has one or more symptoms associated with irritable bowel syndrome.

8. The method according to claim 7, wherein the one or more symptoms associated with irritable bowel syndrome are selected from, diarrhoea, constipation, abdominal cramps and abdominal pain.

9. The method according to claim 1, wherein the dietary intervention is a low wheat diet.

10. The method according to claim 1, wherein the dietary intervention is a low FODMAP diet.

11. A method of determining the probability that an individual with irritable bowel syndrome will respond to dietary intervention, the method comprising the steps of:
   i) analysing a stool sample collected from said individual to determine whether a cyclohexane carboxylic acid compound is present; and
   ii) if a cyclohexane carboxylic acid compound is present in step i), determining the amount of the cyclohexane carboxylic acid compound that is present and comparing the amount detected with a control value;
   wherein the presence of an increased amount of the cyclohexane carboxylic acid compound compared to the control value is indicative of an increased probability that the individual will respond to dietary intervention; and wherein the cyclohexane carboxylic acid compound is one or more of a cyclohexane carboxylic acid and/or a cyclohexane carboxylic acid ester.

12. The method according to claim 11, wherein the cyclohexane carboxylic acid compound is cyclohexane carboxylic acid and/or a cyclohexane carboxylic acid (1-4C) alkyl ester.

13. The method according to claim 11, wherein the cyclohexane carboxylic acid compound is selected from cyclohexane carboxylic acid methyl ester, cyclohexane carboxylic acid ethyl ester, cyclohexane carboxylic acid propyl ester, and cyclohexane carboxylic acid butyl ester.

14. The method according to claim 13, wherein the cyclohexane carboxylic acid compound is selected from cyclohexane carboxylic acid ethyl ester, cyclohexane carboxylic acid propyl ester and cyclohexane carboxylic acid butyl ester.

15. The method according to claim 11, wherein the step of analysing the stool sample involves detecting whether two or more cyclohexane carboxylic acid compound are present.

16. The method according to claim 11, wherein the presence and amount of the cyclohexane carboxylic acid compound is determined by detecting volatile organic compounds emanating from the stool sample using gas chromatography mass spectrometry (GC-MS).

17. The method according to claim 11, wherein the individual has one or more symptoms associated with irritable bowel syndrome.

18. The method according to claim 17, wherein the one or more symptoms associated with irritable bowel syndrome are selected from, diarrhoea, constipation, abdominal cramps and abdominal pain.

19. The method according to claim 11, wherein the dietary intervention is a low wheat diet.

20. The method according to claim 1, wherein the dietary intervention is a low FODMAP diet.

* * * * *